United States Patent
Vidal et al.

[11] Patent Number: 6,047,861
[45] Date of Patent: Apr. 11, 2000

[54] TWO COMPONENT FLUID DISPENSER

[75] Inventors: Claude Vidal; Russell Redmond; Alan K. Plyley, all of Santa Barbara, Calif.

[73] Assignee: VIR Engineering, Inc., Santa Barbara, Calif.

[21] Appl. No.: 09/060,439

[22] Filed: Apr. 15, 1998

[51] Int. Cl.$^7$ .................................................. B67D 5/52
[52] U.S. Cl. ...................... 222/137; 222/145.5; 222/149; 222/327; 222/391
[58] Field of Search ................................ 222/137, 145.5, 222/145.6, 148, 149, 326, 327, 391, 459

[56] References Cited

U.S. PATENT DOCUMENTS

| | | | |
|---|---|---|---|
| 4,012,822 | 3/1977 | Vrolyk et al. | 222/145.6 |
| 4,040,420 | 8/1977 | Speer | 128/218 M |
| 4,109,653 | 8/1978 | Kozam et al. | 128/288 |
| 4,471,887 | 9/1984 | Decker | 222/149 |
| 4,631,055 | 12/1986 | Redl et al. | 604/82 |
| 4,735,616 | 4/1988 | Eibl et al. | 604/191 |
| 4,743,229 | 5/1988 | Chu | 604/82 |
| 4,826,048 | 5/1989 | Skorka et al. | 222/137 |
| 4,874,368 | 10/1989 | Miller et al. | 604/82 |
| 4,902,281 | 2/1990 | Avoy | 604/191 |
| 4,978,336 | 12/1990 | Capozzi et al. | 604/82 |
| 4,979,942 | 12/1990 | Wolf et al. | 604/83 |
| 5,049,135 | 9/1991 | Davis | 604/181 |
| 5,116,315 | 5/1992 | Capozzi et al. | 222/137 |
| 5,163,584 | 11/1992 | Huber et al. | 222/145.5 |
| 5,180,082 | 1/1993 | Cherfane | 222/145.5 |
| 5,265,761 | 11/1993 | Brown | 222/148 |
| 5,535,922 | 7/1996 | Maziarz | 222/327 |
| 5,887,755 | 3/1999 | Hood, III | 222/145.5 |

FOREIGN PATENT DOCUMENTS 9306940  4/1993  WIPO .................................. 222/137

*Primary Examiner*—Joseph A. Kaufman
*Attorney, Agent, or Firm*—James E. Brunton

[57] ABSTRACT

A two-component fluid dispenser which can accurately mix two liquids of varying viscosity and then precisely deliver the mixture formed in discrete amounts. The mixture of the two components is delivered from a single delivery tube in a manner such that none of the mixture remains within the delivery tube at the completion of each mixing and delivery cycle. In one form of the apparatus, the single delivery tube of the apparatus is operably coupled with conventional hypodermic syringes of various sizes so that different fluids can be mixed in different ratios.

25 Claims, 8 Drawing Sheets

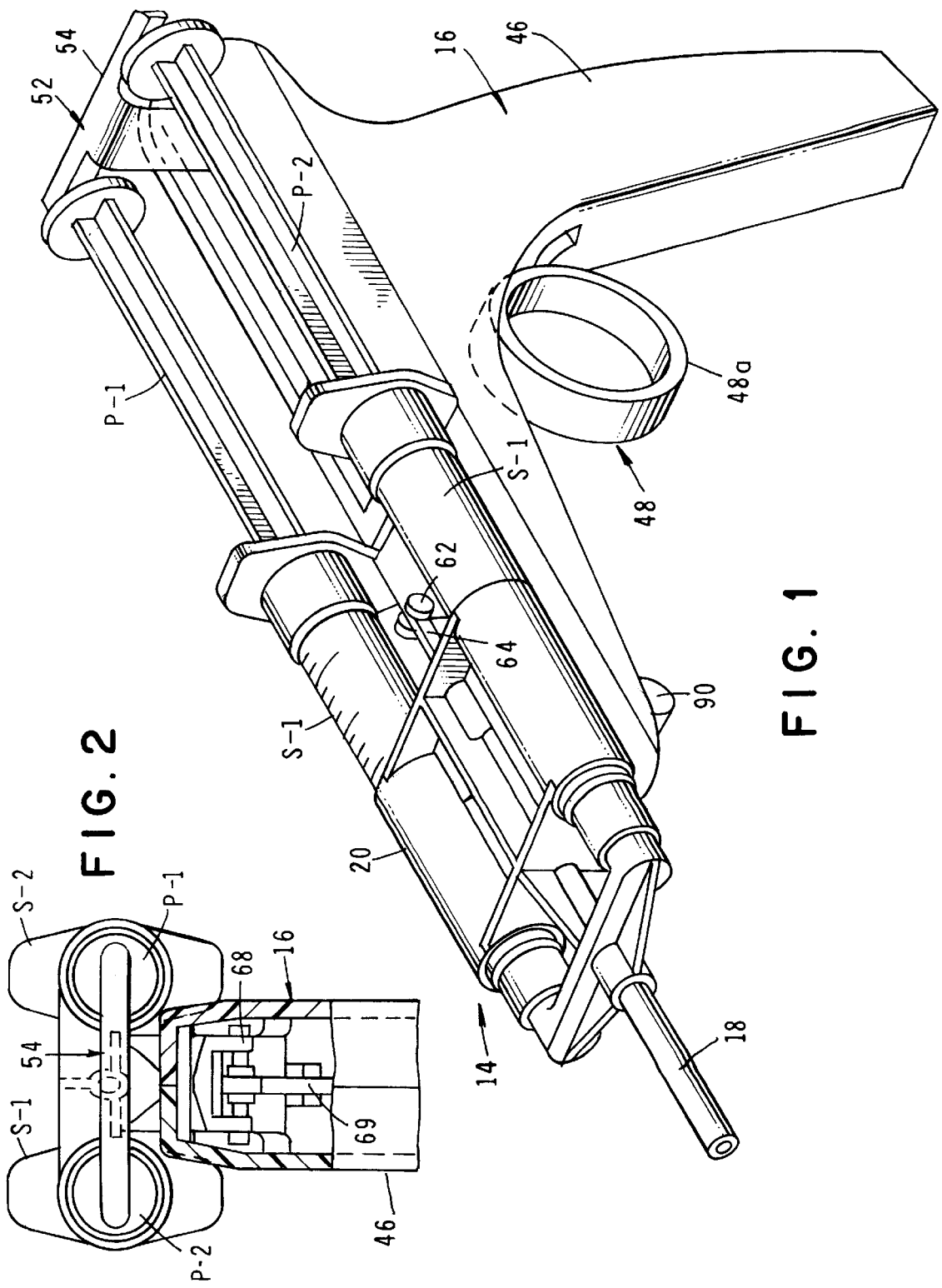

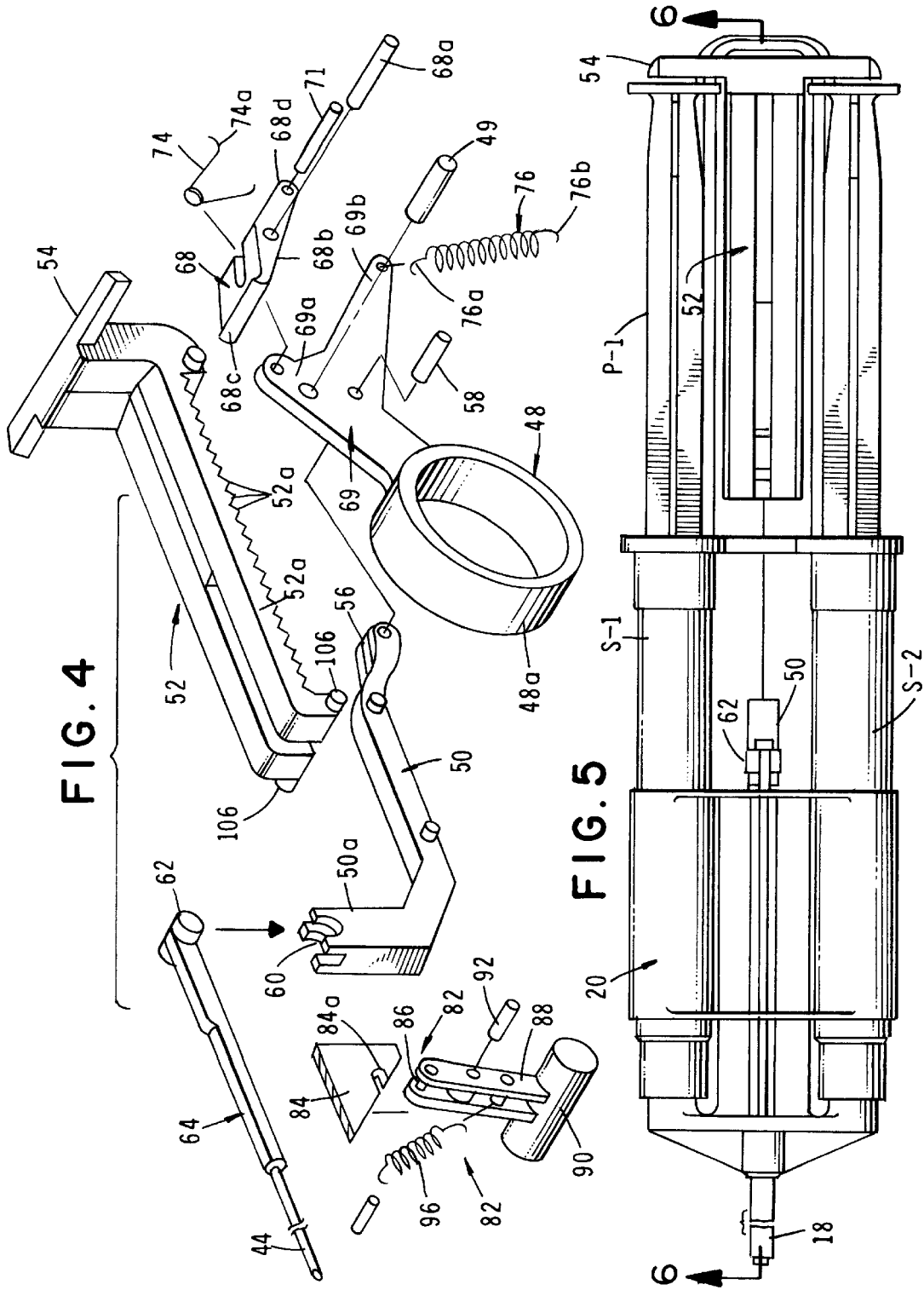

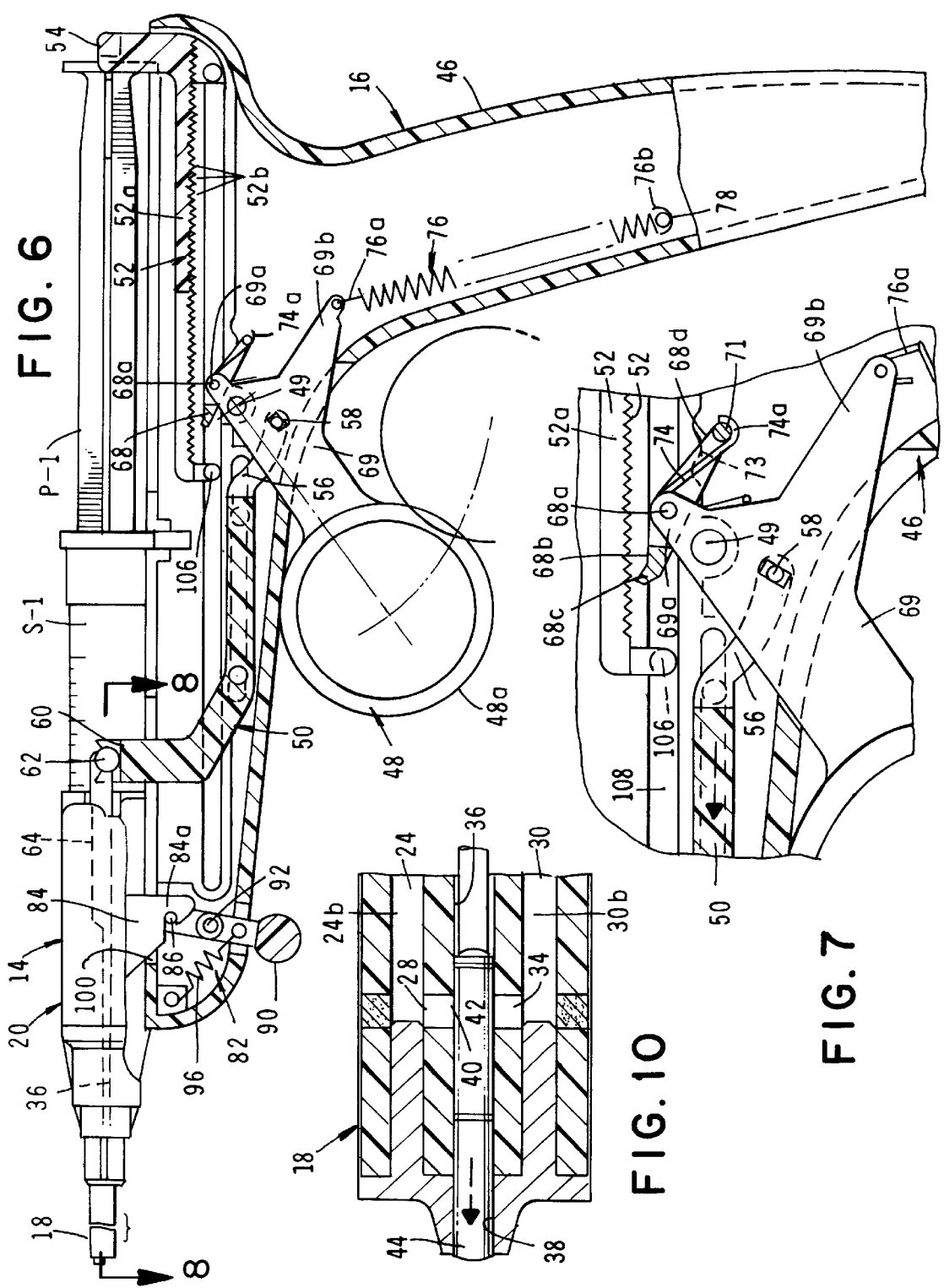

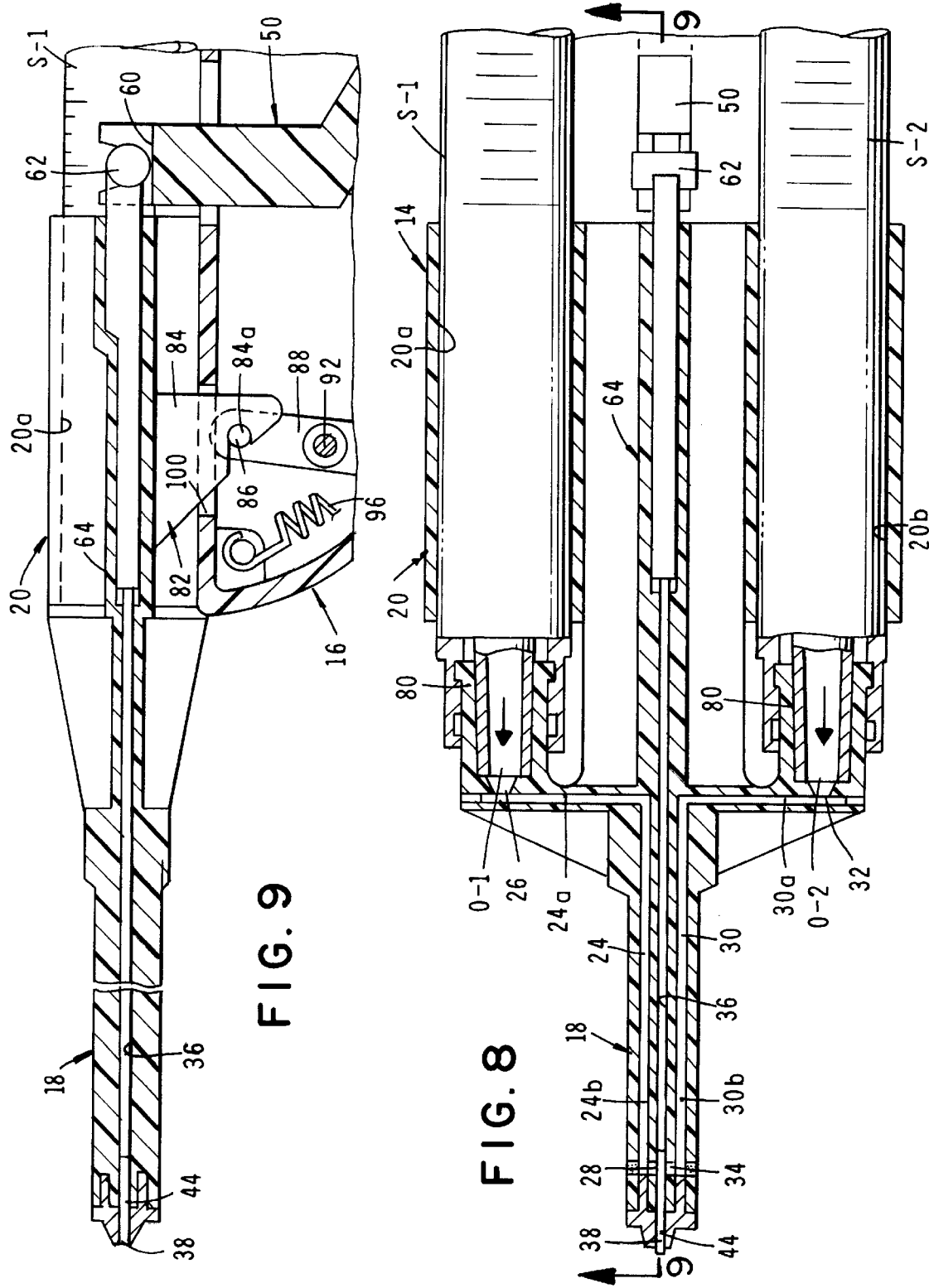

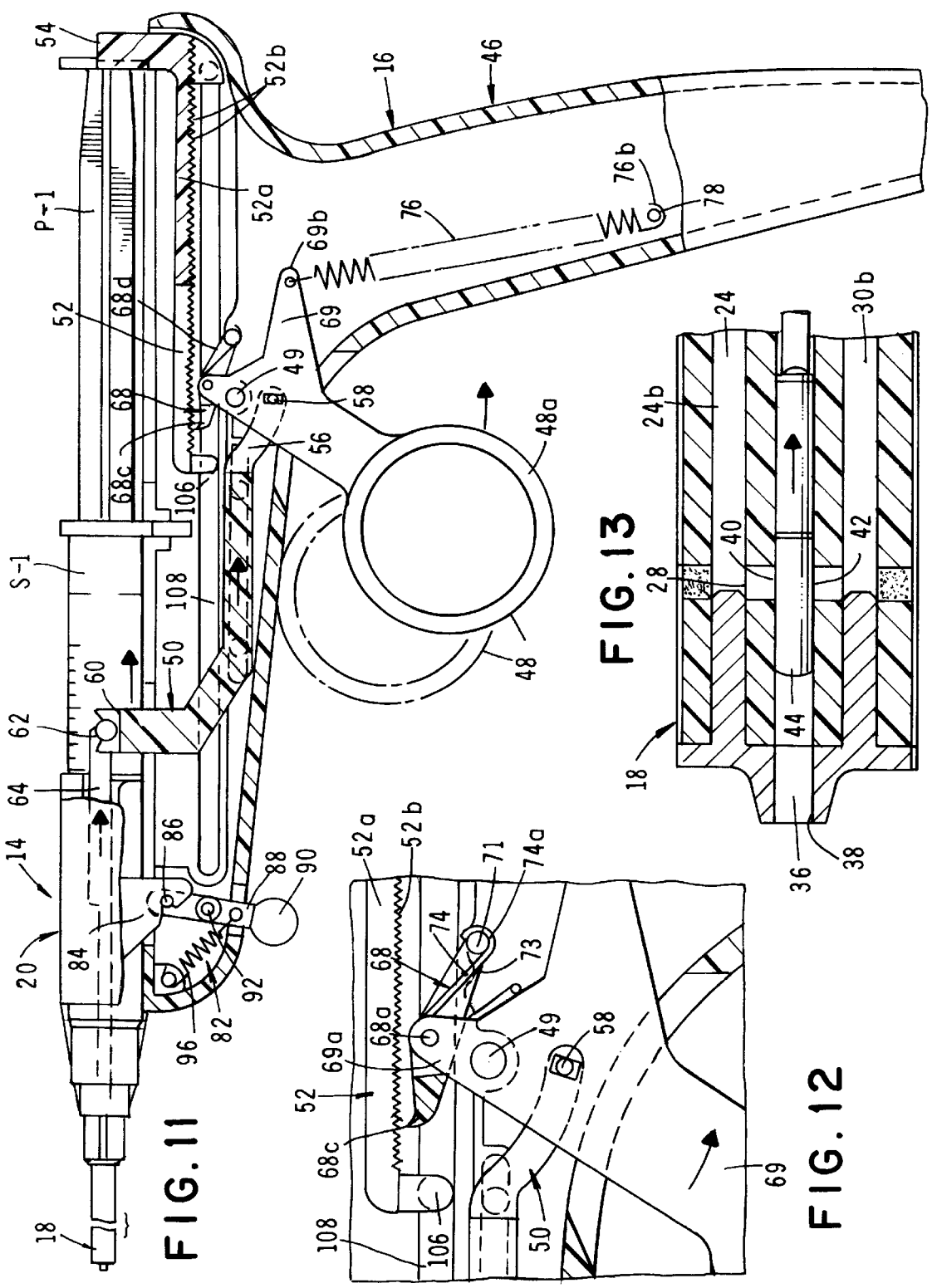

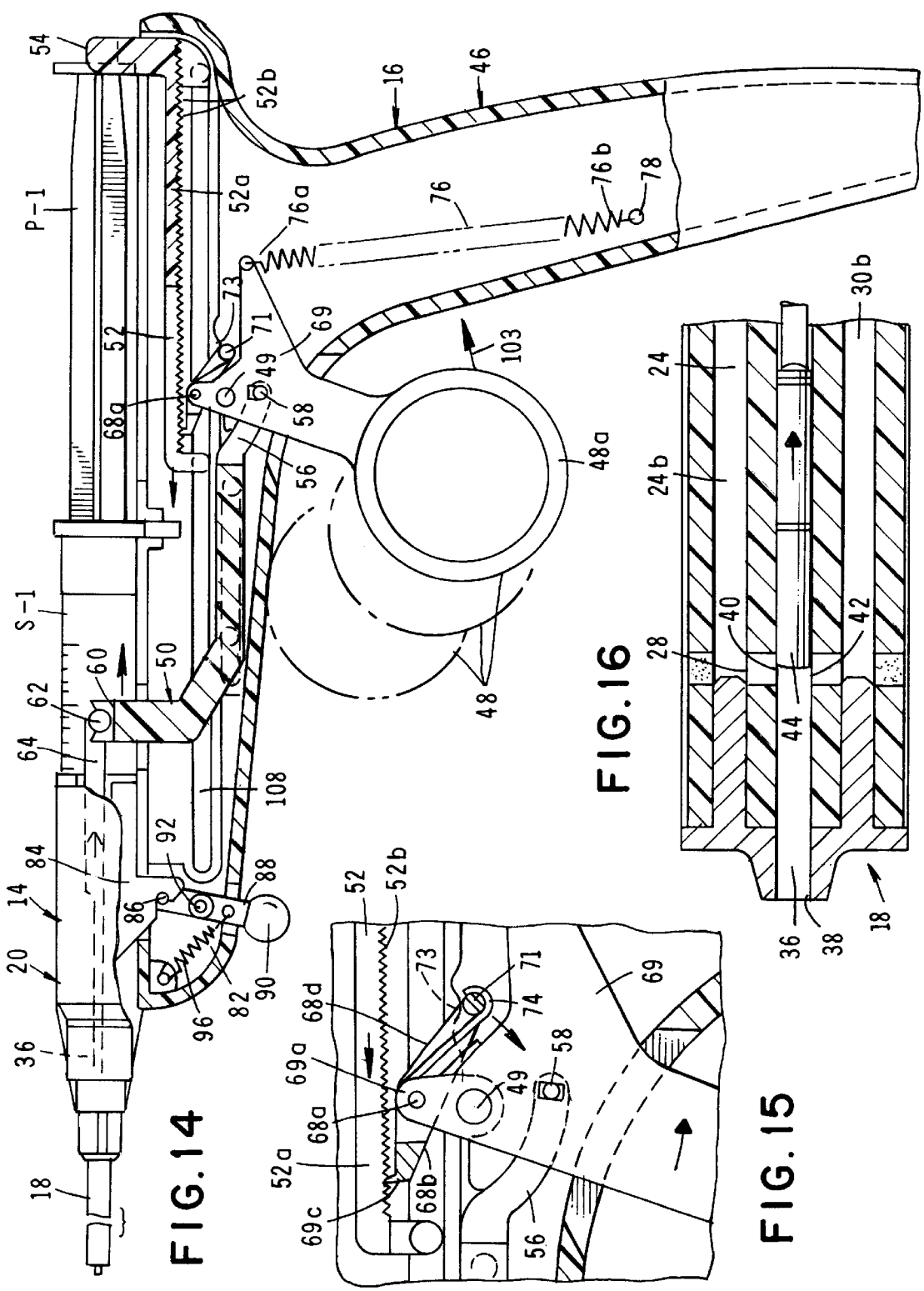

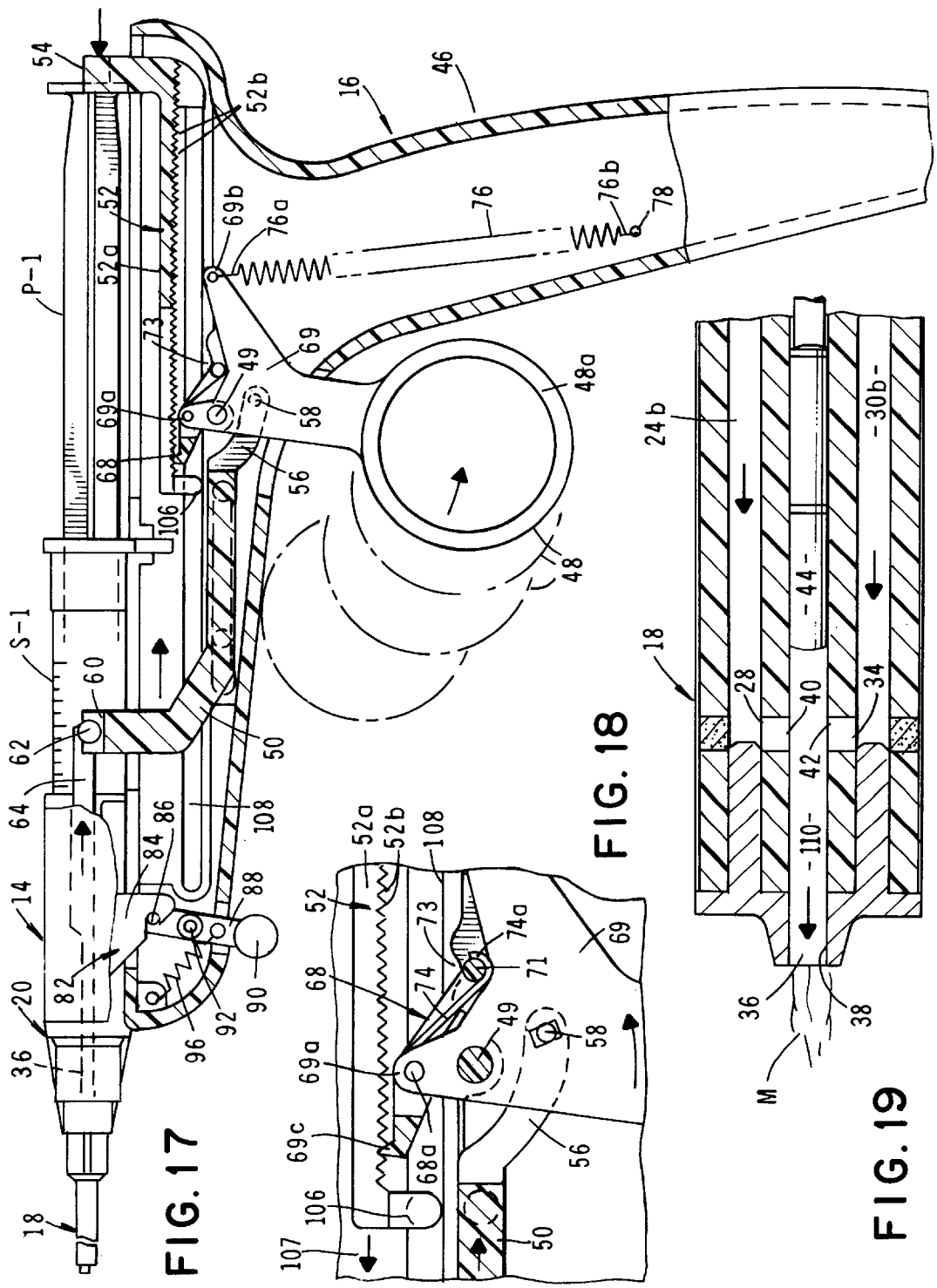

TWO COMPONENT FLUID DISPENSER

BACKGROUND OF THE INVENTION

1. Field of the Invention

The present invention relates generally to a fluid mixing and delivery devices. More particularly, the invention concerns an apparatus for the controlled mixing and incremental delivery of two liquids in a manner such that none of the mixture formed remains within the delivery tube of the apparatus at the end of each delivery cycle.

2. Discussion of the Prior Art

There are a number of situations where it is necessary to separately store two liquid components, to intermix the components and then to controllably dispense the mixture formed. One example of such a situation is found in the adhesive arts wherein, a polymer, such as an oligomer is stored in one container and the cross-linking agent, such as a hardener or curing agent is stored in a separate container. A similar situation exists in those instances wherein the mixing of two components prior to their delivery creates a third chemical with a short pot life. In the medical field a like situation arises when separate components are intermixed to controllably form a mixture such as thrombin-fibrinogen which, following the mixing step, is delivered to an active medical site.

Several devices have been suggested in the past for intermixing and then delivering separate liquid components. However, these devices have typically exhibited various drawbacks. For example, devices which have been suggested for the mixing and delivery of fibrin glue during surgery have traditionally exhibited undesirable clogging. In another vein, many of the prior art devices which attempt to mix and then deliver separate low viscosity liquid chemicals fail to achieve the desired mixture ratio of the components. Additionally, many of the prior art mixing and delivery devices tend to be bulky, unwieldy and quite often require the use of two hands to operate the device.

One type of prior art mixing and delivery device is disclosed in U.S. Pat. No. 5,049,135 issued to Davis. This device comprises a medical lavage syringe apparatus which includes a housing having tabs which engage longitudinal followers on irrigation and aspiration plungers for causing the plungers to stay in a particular rotational orientation during their operation. The aspiration plunger includes a latching surface which engages a tab surface when the aspiration plunger is rotated in an inserted position for locking the aspiration plunger in the inserted position. The plungers include stop surfaces which contact tab surfaces for preventing the plungers from leaving their respective cylinders.

Another type of prior art two component syringe delivery system is disclosed in U.S. Pat. No. 4,979,942 issued to Wolf et. al. The Wolf et. al. system permits the simultaneous delivery of two reactive fluids from a pair of syringes to a delivery site. In one embodiment of the invention a length of tubing exits one syringe and passes through a cannula exiting from the other syringe, to deliver both fluids, separately, but in a controlled volume and space to the delivery site. Alternately, the fluids can mix within the cannula, but its configuration prevents clogging at the delivery site.

The prior art patent to Miller et al, U.S. Pat. No. 4,874,368 discloses a fibrin glue delivery system which comprises a pair of syringe tubes that can be actuated by plungers simultaneously or independently, a connecting member which holds the syringe tubes in parallel alignment and a needle assembly which ensures the components in the syringe bodies will not be commingled until they reach the treatment site.

The present invention seeks to overcome many of the drawbacks of the prior art, two component syringe delivery systems by providing an elegantly simple apparatus which can accurately dispense discrete amounts of two controllably intermixed components. More particularly, the apparatus of the inventions is uniquely designed to automatically clear the delivery tube of the device of any mixture at the completion of each delivery cycle. Accordingly, unlike many of the prior art devices, when the apparatus of the present invention is used to dispense adhesives and surgical glues, the delivery tube of the device never becomes clogged.

SUMMARY OF THE INVENTION

It is an object of the present invention to provide a two component syringe type fluid dispenser which can accurately mix two liquids of varying viscosity and then precisely deliver the mixture formed in discrete amounts.

Another object of the invention is to provide a two component fluid dispenser of the aforementioned character in which the mixture of the two components is delivered from a single delivery tube in a manner such that none of the mixture remains within the delivery tube at the completion of each mixing and delivery cycle.

Another object of the invention is to provide a two component fluid dispenser of the type describe in which the single delivery tube of the apparatus can readily be operably coupled with fluid sources such as conventional hypodermic syringes of various sizes so that different fluids can be mixed in different ratios.

Another object of the invention is to provide a two component fluid dispenser in which the fluid sources such as hypodermic syringes are securely held in place within a holder which allows for the simultaneous delivery of the two components as a result of controlled pressures being exerted on the fluid expelling plungers of the two syringes thereby permitting the precise dispensing of discrete amounts of the mixture of the two components.

Another object of the invention is to provide a fluid dispenser of the character described in the preceding paragraphs which permits the two components to be delivered to be intermixed immediately prior to the delivery of the mixture from the outlet port of the delivery tube of the device.

Another object of the invention is to provide a fluid dispenser of the character described which is lightweight, is easy to use with one hand and one in which the delivery mechanism is reusable.

Still another object of the invention is to provide a two component fluid dispenser of the class described which can be produced in high volume at relatively low cost.

These and other objects of the invention are realized by providing a novel apparatus in which two fluid sources such as two conventional hypodermic syringes can be locked in place within a disposable body which, in turn, can be locked into position within a reusable operating mechanism. The operating mechanism controllably acts upon the fluid expelling plungers of the syringes to first precisely meter the fluid components contained therein into the mixing chamber of the device and then to deliver discrete amounts of the mixture formed from a single delivery tube. The disposable body of the apparatus is constructed so that the two syringes can be easily and securely connected to the body via conventional luer lock fittings. Delivery of the component mixture is accomplished by manipulating a novel finger operated trigger mechanism which is mounted proximate a specially configured pistol grip type handle that can be comfortably gripped by the operator using only one hand. The trigger mechanism initially operates a novel reciprocating valve which permits the components which are to be intermixed to flow into a mixing chamber. After opening the valve, continued movement of the trigger will cause the mixture formed to be controllably dispensed from the single delivery tube of the apparatus. Following each delivery cycle the valve will automatically return to its starting position causing any mixture remaining in the delivery tube to be completely expelled from the delivery tube.

BRIEF DESCRIPTION OF THE DRAWINGS

FIG. 1 is a generally perspective view of one form of the syringe type mixing and delivery apparatus of the present invention.

FIG. 2 is a fragmentary rear view of the upper portion of the apparatus shown in FIG. 1 partly in cross-section to show internal construction.

FIG. 4 is a generally perspective, exploded view of the valving mechanism and the operating mechanism of the apparatus of one form of the invention.

FIG. 5 is a is a top plan view of the apparatus shown in FIG. 1.

FIG. 6 is a is a cross-sectional view taken along lines 6—6 of FIG. 5.

FIG. 7 is an enlarged, fragmentary side elevational view of the operating pawl and pawl engaging rack of one form of the operating means of the invention.

FIG. 8 is an enlarged cross-sectional view taken along lines 8—8 of FIG. 6.

FIG. 9 is cross-sectional view taken along lines 9—9 of FIG. 8.

FIG. 10 is a greatly enlarged, fragmentary cross-sectional view of the output end of the delivery tube of the apparatus showing the arrangement of the various fluid flow passageways formed in the delivery tube.

FIG. 11 is a side elevational, cross-sectional view similar to FIG. 6, but showing the trigger mechanism moved from the first position to a second position.

FIG. 12 is a fragmentary view similar to FIG. 7 further illustrating the rearward movement of the trigger mechanism in a direction toward the second position.

FIG. 13 is a fragmentary cross-sectional view similar to FIG. 10 showing further movement of the valve member in response to further movement of the trigger mechanism.

FIG. 14 is a side elevational cross-sectional view similar to FIG. 11, but showing the trigger mechanism moved from the second position shown in FIG. 11 to a third position.

FIG. 15 is a fragmentary view similar to FIG. 12 illustrating further rearward movement of the trigger mechanism.

FIG. 16 is a fragmentary cross-sectional view similar to FIG. 13 showing the continual movement of the valve member in response to the further movement of the trigger mechanism.

FIG. 17 is a side elevational, cross-sectional view similar to FIG. 14 but showing the trigger mechanism moving into a fourth operating position.

FIG. 18 is a fragmentary view similar to FIG. 15 further illustrating the continual rearward movement of the trigger mechanism.

FIG. 19 is a fragmentary, cross-sectional view similar to FIG. 16 showing continued movement of the trigger mechanism and the resultant movement of the operating pawl of the apparatus into engagement with the elongated toothed rack of the apparatus which engages the fluid expelling plungers of the two syringe components.

DESCRIPTION OF THE INVENTION

Figure 3:
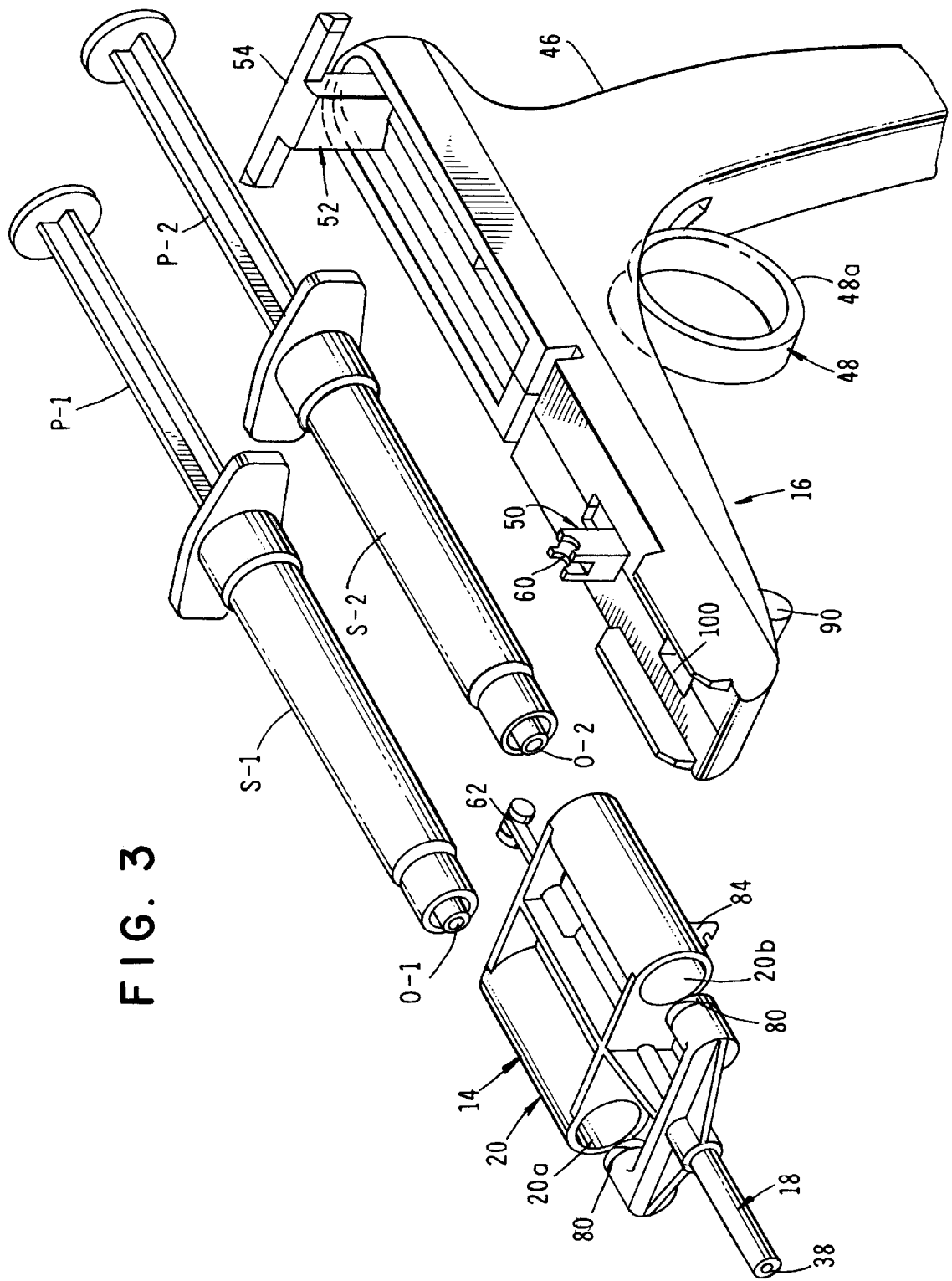
FIG. 3 is a generally perspective exploded view of the apparatus shown in FIG. 1.

Referring to the drawings and particularly to FIGS. 1 through 6, one form of the mixing and delivery apparatus of the present invention is there illustrated. The apparatus functions to mix a first fluid contained within a first fluid source shown here as a first syringe S-1, having a fluid outlet 0-1, with the fluid contained within a second fluid source, shown here as a second syringe S-2 having a fluid outlet 0-2. (See FIGS. 3 and 5)

As best seen in FIG. 3, in addition to the first and second fluid sources, the apparatus comprises two major cooperating components, namely a delivery means, or delivery assembly 14, and an operating means or operating assembly 16. The delivery means and the operating means are releasably interconnected by latching means, the character of which will presently be described. Delivery assembly 14 includes a delivery tube 18 which houses a novel flow control means for controlling fluid flow through the delivery tube and a syringe receiving body 20. Syringe receiving body 20 includes a first chamber 20a, for telescopically receiving first syringe, S-1 and a second chamber 20b for telescopically receiving second syringe S-2 (FIG. 8). As shown in FIG. 8, syringe receiving body 20 also includes a first passageway 24 having a transverse segment 24a provided with an inlet 26 in fluid communication with outlet 0-1 of first syringe S-1 and a longitudinally extending segment 24b having an outlet 28. Body 20 further includes a second passageway 30 having a transverse segment 30a provided with an inlet 32 in fluid communication with outlet 0-2 of second syringe S-2 and a longitudinally extending segment 30b having an outlet 34. (see also FIG. 10).

As indicated in FIGS. 8 and 10, delivery tube 18 is integrally formed with the syringe receiving body 20 and includes, in addition to passageways 24 and 30, a third centrally located fluid delivery passageway 36 having an outlet port 38 (FIG. 10), a first inlet 40 in communication with outlet 28 of passageway 24 and a second inlet 42 in communication with outlet 34 of passageway 30.

The previously mentioned flow control means of the invention functions to control fluid flow from outlets of 28 and 34 of passageways 24 and 30 respectively into the third passageway 36. Additionally, a valve member 44 which comprises a part of the flow control means uniquely functions to clear residue from the outlet port 38 of the third passageway of the delivery tube following each mixing and delivery cycle. The manner in which valve member 44 functions to accomplish this important clearing step will presently be described.

Turning particularly to FIGS. 4, 7 and 10, it is to be noted that valve member 44 is movable within third passageway 36 from the first position shown in FIG. 10 wherein it blocks flow of fluid into third passageway 36 to a second intermediate position shown in FIG. 13 and finally into a third retracted position shown in FIGS. 16 and 19 wherein the valve member permits fluid flow into the third delivery passageway via first and second inlets 40 and 42.

The second major component of the apparatus of the invention, namely the operating means or operating assembly 16, functions to operate the flow control means of the invention and further functions to operate the fluid expelling plungers P1 and P2 of the first and second syringes S-1 and S-2 respectively (FIG. 3). More particularly, the operating means operates the fluid expelling plungers of the two syringes in a manner to controllably cause fluid within first syringe S-1 to flow toward the outlet 0-1 thereof and to cause fluid within the second syringe S-2 to controllably flow toward the outlet 0-2 of this syringe. As best seen in FIGS. 3 and 6, the operating means here comprises gripping means, which includes a pistol-like grip 46 for gripping with one hand. The operating means also includes a trigger means, which comprises a trigger mechanism 48 that is pivotally interconnected with handle 46 and is operable by the index finger of the user. As illustrated in FIG. 4, 11, 16 and 17, trigger mechanism 48 is pivotally movable about a pivot pin 49 from a first position shown in FIG. 6 to a second intermediate position shown in FIG. 11 to a third position shown in FIG. 16 and finally into a fourth position shown in FIG. 17.

As best seen in FIGS. 4,6 and 7, trigger mechanism 48 is operably coupled with both a generally "L" shaped valve operating mechanism 50 and with a plunger operating mechanism 52, which includes a "T"-shaped bar 54 for engaging plungers P-1 and P2 of the first and second syringes S-1 and S-2, (FIG. 1). Valve operating mechanism 50 includes at one end a downwardly curved, yoke-like portion 56 which is pivotally connected to trigger mechanism 48 by a pin 58. Provided proximate the opposite end 50*a* of member 50 is an upstanding cradle-like portion 60 which receives the inboard end 62 of an elongated valving component 64 of which the previously mentioned valve member 44 forms an integral part,(FIG. 4).

In the present form of the invention, the plunger operating means or mechanism 52 comprises an elongated toothed rack member 52*a* having a plurality of longitudinally spaced teeth 52*b* which, in a manner presently to be described, are engagable by a wing-like pawl 68 which forms a part of trigger mechanism 48. More particularly, trigger mechanism 48 includes a finger engagable trigger member 48*a*, an irregularly shaped connector plate 69 and the wing-shaped connector pawl 68 which is pivotally connected to connector plate 69 (FIG. 4). Connector plate 69 includes an upwardly extending finger 69*a* to which pawl 68 is pivotally connected by a pin 68*a* and a downwardly extending finger 69*b*. Pawl 68 includes a body portion 68*b* having a tooth engaging, hook-like first end 68*c* and an opposite end 68*d* which is apertured to receive a small pin 71, (FIG. 4).

Referring particularly to FIGS. 14, 16, 17 and 18 it is to be observed that as trigger member 48*a* is moved toward the third position shown in FIG. 14, end 68*c* of pawl 68 will be urged into mating engagement with the teeth 52*b* of rack member 52*a* due to the upward pivotal movement of finger 69*a* and the engagement of pin 71 with a surface 73 provided on the operating means. (See particularly FIG. 15). As pin 71 moves into engagement with a downwardly extending cam like surface 73 a first biasing means or small spring 74 which is connected to pivot pin 68*a*, will be yieldably deformed in the manner shown in FIG. 15 and the hook-like end 68*c* of pawl 68 will move into pressural engagement with teeth 52*b*. As best seen in FIG. 4, spring 74 has a central portion which circumscribes pivot pin 68*a* and a downwardly extending, hook-like end portion 74*a* which partially circumscribes pin 71. With this construction, pawl 68 is continuously urged out of engagement with teeth 52*b* (see FIG. 7) until pin 71 cammingly engages downwardly extending, curved surface 73 in the manner shown in FIG. 15.

A second biasing means shown here as an elongated coil spring 76 functions to continuously urge trigger 48*a* toward its starting position shown in FIG. 6. The inboard or upper end 76*a* of spring 76 is connected to finger 69*b* of connector plate 69 and its opposite end 76*b* connected to a pin 78 which is secured to handle 46 (see FIGS. 4 and 6). With this construction, as trigger 48*a* is moved from the starting position shown in FIG. 6, to the finishing position shown in FIG. 17, spring 76 will be yieldably elongated so that upon release of trigger 48*a*, the trigger will automatically return to the starting position shown in FIG. 6.

With the component parts of the apparatus in the position shown in FIG. 3, the apparatus is assembled by first inserting syringes S-1 and S-2 into chambers 20*a* and 20*b* so that they can be interconnected with male luer connectors 80 which are provided at the forward portion of housing 20 (FIG. 8). With syringes S-1 and S-2 suitably interconnected with luer connectors 80, the assemblage thus formed is next interconnected with operating mechanism 16. To accomplish this interconnection, latching means are provided to releasably interconnect the deliverymeans and the operating means. This latching means here comprises a latch mechanism generally designated in FIG. 4 by the numeral 82. Mechanism 82 includes a downwardly extending, generally triangular shaped tab 84 which is integrally formed with housing 20 (FIG. 9). Connected to tab 84 by a connector pin 86 is a latch arm 88, which is provided at its lower end with transversely extending latch bar 90. Latch arm 88 is pivotally interconnected with the body of operating mechanism 16 by means of a pivot pin 92. A third biasing means, shown here as a coil spring 96, continuously urges pin 86 of the latch mechanism into engagement with a notch 84*a* provided in tab 84, (FIGS. 6 and 9).

With the construction thus described, as the assemblage made up of delivery component 14 and syringes S-1 and S-2 is mated with the operating assembly 16, tab 84 is received within a slot 100 formed in the body of the operating mechanism (see FIGS. 3 and 9). A downward force exerted upon the assemblage will cause tab 84 to slidably engage pin 86 causing the latching arm 88 to move to the right as viewed in FIG. 6. As housing 20 of the delivery component seats within the forward portion of operating mechanism 16, spring 96 will urge pin 86 to snap into slot 84*a* thereby lockably interconnecting body 20 with the operating mechanism in the manner shown in FIG. 6. With housing 20 seated within operating mechanism 16 in the manner shown in FIG. 6, the plungers P-1 and P-2 of syringes S-1 and S-2 appropriately seat within the operating mechanism in a manner such that the ends of the fluid expelling plungers P-1 and P-2 will move into close proximity with T-bar 54 of operating mechanism 52. It is apparent that, when desired, the assemblage made up of housing 20 and syringes S-1 and S-2 can be removed from the operating mechanism by exerting a rearward force on transverse bar 90 of the latching mechanism so as to move pin 86 out of slot 84*a* so that the upper delivery assemblage can be separated from the operating mechanism.

With the delivery means of the apparatus interconnected with the operating means, and with trigger 48 in its starting position, the hook-like end 68*c* of pawl 68 is located in a spaced apart relationship with tooth rack 52 in the manner best seen in FIG. 7. It is also to be observed that, as shown in FIG. 9, during the mating of the delivery means with the operating means the cradle portion 60 of valve operating mechanism 50 will closely receive end portion 62 of valve member 64 so as to operably interconnect operating mechanism 50 with valve component 64. With the component parts in the assembled position shown in FIG. 6, it is further to be noted that valve member 44 of valving component 64 is in its forward most position blocking fluid flow through inlet ports 40 and 42 leading toward central passageway 36, (See also FIGS. 9 and 10).

Turning now to FIGS. 11 through 13, it can be seen that movement of trigger 48a from the first position shown in FIG. 6 to the second position shown in FIG. 11, will cause rearward movement of valve operating mechanism 50 from the position shown in FIG. 6 to the position shown in FIG. 11. This rearward movement of mechanism 50 will, in turn, cause rearward movement of valve member 44 from the position shown in FIG. 10 to the intermediate position shown in FIG. 13. As indicated in FIG. 12, during this initial movement of the trigger mechanism, pawl 68 remains in a spaced apart location relative to rack 52.

Continued rearward movement of trigger 48a from the position shown in FIG. 11 into the position shown in FIG. 14, will cause further rearward movement, of valve operating component 50 and the concomitant rearward movement of valve member 44 from the position shown in FIG. 13 to the position shown in FIG. 16. With valve member 44 in this latter position, it can be seen that inlets 40 and 42 are opened so as to permit fluid flow from passageways 24b and 30b into central passageway 36. It is also to be noted that the further pivotal movement of trigger 48a to the position shown in FIG. 14 will cause pin 71 of the pawl assembly to move into engagement with surface 73 of the operating mechanism. This, in turn, will cause end 68c of the pawl to move into engagement with the teeth 52b provided on rack 52 against the urging of spring 74. Once the hook-like end 68c of pawl 68 moves into engagement with teeth 52b, a continued rearward movement of trigger 48a in the direction of the arrow 103 of FIG. 14, will cause the component parts of the apparatus to move into the locations shown in FIGS. 17, 18 and 19. More particularly, this further rearward movement of trigger 48a will cause pawl 68 to move rack 52 to the left as viewed in FIGS. 17 and 18 causing T-bar 54 to pressurally engage plungers P-1 and P-2 of the syringes in a manner to urge them inwardly into the fluid reservoirs of syringes S-1 and S-2. This inward movement of the fluid expelling plungers P-1 and P-2 will cause the fluid contained within the syringes to flow through passageways 24b and 30b and then through inlets 40 and 42 into central passageway 36 in the manner indicated in FIG. 19.

Turning once again to FIG. 4, it is to be observed that plunger operating member 52 is provided proximate its forward end with transversely extending guide pins 106 which are arranged to slide along longitudinally extending guide channels 108 provided in the body of operating mechanism 16 (see FIGS. 17 and 18). As trigger 48a moves from the position shown in FIG. 14 to the position shown in FIG. 17, member 52 will be urged forwardly in the direction of the arrow 107 of FIG. 18 causing the mixture of the fluid components contained within syringes S-1 and S-2 to be expelled from outlet port 38 in the manner shown in FIG. 19. This mixture "M" will be expelled from outlet port 38 in an incremental amount corresponding to the extent of forward movement of rack 52 and the concomitant inward movement of fluid expelling plungers P-1 and P-2 into their respective syringe bodies.

When trigger 48a is released, spring 76 will cause the trigger mechanism to immediately return to the original starting position shown in FIG. 6. As trigger mechanism 48 returns to the starting position shown in FIG. 6, it is to be observed that valve operating mechanism 50 will move forwardly of the apparatus causing valve member 44 to once again return to the starting position shown in FIG. 10. Importantly, as valve member 44 moves to the left as viewed in FIG. 10, it will automatically clear outlet port 38 of all of the fluid mixture "M" which was formed in the mixing chamber 110. Simultaneously, with the return of the valve member 44 to its starting position, spring 74 will urge pawl 68 into a spaced apart location relative to plunger operating member 52.

With the various components of the apparatus returned to their starting configuration as shown in FIG. 6, the dispensing cycle can be repeated as many times as required to dispense the required number of increments of mixture "M" from the delivery tube in the manner shown in FIG. 19. As previously mentioned, after each dispensing cycle, valve member 44 will be returned to the starting position shown in FIG. 10 thereby effectively cleaning the delivery passageway 36 and the outlet 38 from all residue of mixture "M".

Having now described the invention in detail in accordance with the requirements of the patent statutes, those skilled in this art will have no difficulty in making changes and modifications in the individual parts or their relative assembly in order to meet specific requirements or conditions. Such changes and modifications may be made with out departing from the scope and spirit of the invention, as set forth in the following claims.

We claim:

1. A mixing and delivery device for use by an operator to mix together a first and second fluids and then to deliver the mixture formed, said device comprising:
   (a) a delivery tube having:
      (i) first and second fluid passageways, each said fluid passageway having an inlet and an outlet; and
      (ii) a third fluid passageway having an inlet in communication with said outlet of each of said first and second fluid passageways, said third fluid passageway having an outlet port;
   (b) a first fluid source for delivering a first fluid to said inlet of said first passageway, said first fluid source comprising a first syringe having a fluid outlet and a fluid expelling plunger;
   (c) a second fluid source for delivering a second fluid to said inlet of said second fluid passageway, said second fluid source comprising a second syringe having a fluid outlet and a fluid expelling plunger; and
   (d) fluid flow control means operably associated with said delivery tube for controlling fluid flow through said outlets of said first and second passageways of said delivery tube, said fluid flow control means including a valve member movable within said third passageway to clear residue from said outlet port of said third passageway.

2. A device as defined in claim 1 further including operating means operably associated with said fluid flow control means for operating said fluid control means, said operating means including a plunger engaging member for moving said fluid expelling plungers of said first and second syringes to cause fluid within said first syringe to flow into said first fluid passageway of said delivery to tube and to cause fluid within said second syringe to flow into said second fluid passageway of said delivery tube.

3. A device as defined in claim 2 in which said operating means further includes a valve operating mechanism for moving said valve member relative to said delivery tube.

4. A device as defined in claim 3 in which said valve operating mechanism moves said valve member within said third fluid passageway of said delivery tube from a first closed position closing each said outlet of each said first and second fluid passageway to a second intermediate position and then to a third open position opening each said outlet of each said first and second fluid passageway.

5. A device as defined in claim 4 in which said valve member includes a distal portion for clearing residue from said outlet port of said third passageway of said delivery tube.

6. A device as defined in claim 4 in which said operating means includes trigger means connected to said valve operating mechanism, said trigger means being movable from a first position to a second position to move said valve member from said first position to said second intermediate position.

7. A device as defined in claim 6 in which said trigger means is movable from said second position to a third position to move said valve member from said intermediate position to said third open position.

8. A device as defined in claim 7 in which said trigger means is movable from said third position to a fourth position to move the fluid expelling plungers of the first and second syringes toward the fluid outlets thereof whereby fluid within the syringes will be caused to flow into said third passageway of said delivery tube via said outlets of said first and second passageways.

9. A device as defined in claim 8 in which said plunger engaging member is operable by said trigger means when said trigger means is moved from said third position toward said fourth position.

10. A device as defined in claim 9 in which said plunger engaging member comprises a toothed rack portion and in which said trigger means includes a pawl engagable with said toothed rack portion upon said trigger means being moved toward said third position.

11. A device as defined in claim 9 in which said operating means further includes biasing means connected to said trigger means for continuously urging said valve member toward said first closed position.

12. A mixing and delivery device for use by an operator to mix together first and second fluids contained in first and second syringes, each having fluid outlets and then to deliver the mixture formed, said device comprising:

(a) a delivery tube having:
  (i) first and second fluid passageways, each said fluid passageway having an inlet and an outlet; and
  (ii) a third fluid passageway having an inlet in communication with said outlet of each of said first and second fluid passageways, said third fluid passageway having an outlet port;
(b) syringe receiving means for placing the fluid outlet of the first syringe in communication with said inlet of said first fluid passageway and for placing the fluid outlet of the second syringe in communication with said inlet of said second fluid passageway; and
(c) fluid flow control means operably associated with said delivery tube for controlling fluid flow through said outlets of said first and second passageways of said delivery tube, said fluid flow control means including a valve member movable within said third passageway to clear residue from said outlet port of said third passageway.

13. A device as defined in claim 12 further including operating means operably associated with said fluid flow control means for operating said fluid control means, said operating means including a plunger engaging member for moving fluid expelling plungers of said first and second syringes to cause fluid within said first syringe to flow into said first fluid passageway of said delivery to tube and to cause fluid within said second syringe to flow into said second fluid passageway of said delivery tube.

14. A device as defined in claim 13 in which said operating means further includes a valve operating mechanism for moving said valve member relative to said delivery tube.

15. A device as defined in claim 14 in which said valve operating mechanism moves said valve member within said third fluid passageway of said delivery tube from a first closed position closing each said outlet of each said first and second fluid passageway to a second intermediate position and then to a third position opening each said outlet of each said first and second fluid passageway.

16. A device as defined in claim 15 in which said valve member includes a distal portion for clearing residue from said outlet port of said third passageway of said delivery tube.

17. A mixing and delivery device for mixing a first fluid contained within a first syringe having a fluid outlet and a fluid expelling plunger with a second fluid contained within a second syringe having a fluid outlet and a fluid expelling plunger and then for delivering the mixture formed, said device comprising:

(a) a delivery means for delivering the mixture of the first and second fluids comprising:
  (i) a syringe receiving body having:
    a. a first chamber for receiving the first syringe;
    b. a second chamber for receiving the second syringe.
    c. a first passageway having an outlet and an inlet in fluid communication with said outlet of the first syringe when the first syringe is disposed within said first chamber; and
    d. a second passageway having an outlet and an inlet in fluid communication with said outlet of the second syringe when the second syringe is disposed within said second chamber;
  (ii) a delivery tube connected to said syringe receiving body, said delivery tube including:
    a. a first delivery passageway having a fluid outlet and a fluid inlet in communication with said outlet of said first passageway of said syringe body;
    b. a second delivery passageway having a fluid outlet and a fluid inlet in communication with said outlet of said second passageway of said syringe body;
    c. a third delivery passageway having an outlet port; a first inlet in communication with said outlet of said first delivery passageway of said delivery tube; and a second inlet in communication with said outlet of said second delivery passageway of said delivery tube;
  (iii) fluid flow control means operably associated with said delivery tube for controlling fluid flow from said outlets of said first and second delivery passageways of said delivery tube, said fluid flow control means comprising a valve member movable within said third delivery passageway for clearing said outlet port of said third delivery passageway of said delivery tube, said valve member being movable from a first position blocking fluid flow into said third delivery passageway to a second intermediate position and then to a third position permitting fluid flow into said third delivery passageway via said first and second inlets of said third delivery passageway; and
(b) operating means operably associated with said fluid flow control means for operating said fluid flow control means, said operating means including a plunger engaging member for engaging the fluid expelling plungers of the first and second syringes to cause fluid within the first syringe to flow toward the outlet thereof and to cause fluid within the second syringe to flow toward the outlet thereof.

18. A device as defined in claim 17 in which said operating means further includes a valve operating member and trigger means connected to said valve operating mechanism for moving said valve member from said first position to said second intermediate position, said trigger means being movable from a first position, to a second position, to a third position and then to a fourth position.

19. A device as defined in claim 18 in which said trigger means also functions to move said valve mechanism from said intermediate position to said open position as said trigger means moves to said third position, whereby fluid within the syringes will be caused to flow into said third passageway of said delivery tube via said outlets of said first and second passageways.

20. A device as defined in claim 19 in which said plunger engaging means is operable by said trigger means upon said trigger means moving from said third position toward said fourth position.

21. A device as defined in claim 20 in which said plunger engaging means comprises a toothed rack member and in which said trigger means includes a pawl engagable with said toothed rack member as said trigger means moves toward said fourth position.

22. A device as defined in claim 20 in which said operating means further includes biasing means connected to said trigger means for yieldably resisting movement of said trigger means from said first position thereof.

23. A mixing and delivery device for mixing a first fluid contained within a first syringe having a fluid outlet and a fluid expelling plunger with a second fluid contained within a second syringe having a fluid outlet and a fluid expelling plunger and then for delivering the mixture formed, said device comprising:

(a) a delivery means for delivering the mixture of the first and second fluids comprising:
 (i) a syringe receiving body having:
  a. a first chamber for receiving the first syringe;
  b. a second chamber for receiving the second syringe;
  c. a first passageway having an outlet and an inlet in fluid communication with said outlet of the first syringe when the first syringe is disposed within said first chamber; and
  d. a second passageway having an outlet and an inlet in fluid communication with said outlet of the second syringe when the second syringe is disposed within said second chamber;
 (ii) a delivery tube connected to said syringe receiving body, said delivery tube including:
  a. a first delivery passageway having a fluid outlet and a fluid inlet in communication with said outlet of said first passageway of said syringe body;
  b. a second delivery passageway having a fluid outlet and a fluid inlet in communication with said outlet of said second passageway of said syringe body;
  c. a third delivery passageway having an outlet port; a first inlet in communication with said outlet of said first delivery passageway of said delivery tube; and a second inlet in communication with said outlet of said second delivery passageway of said delivery tube;
 (iii) fluid flow control means operably associated with said delivery tube for controlling fluid flow from said outlets of said first and second delivery passageways of said delivery tube, said fluid flow control means comprising a valve member movable within said third delivery passageway for clearing said outlet port of said third delivery passageway of said delivery tube, said valve member being movable from a first position blocking fluid flow into said third delivery passageway to a second intermediate position and then to a third position permitting fluid flow into said third delivery passageway via said first and second inlets of said third delivery passageway; and (b) operating means operably associated with said fluid flow control means for operating said fluid flow control means, said operating means including:
 (i) a plunger engaging member for engaging the fluid expelling plungers of the first and second syringes to cause fluid within the first syringe to flow toward the outlet thereof and to cause fluid within the second syringe to flow toward the outlet thereof;
 (ii) a valve operating mechanism for moving said valve member from said first position to said second intermediate position; and
 (iii) trigger means connected to said valve operating mechanism for moving said valve operating mechanism; said trigger means including a trigger member movable from a first position to a second position to a third position and to a fourth position; and (c) latching means for releasably interconnecting together said delivery means and said operating means.

24. A device as defined in claim 23 in which said valve operating means also functions to move said valve mechanism from said intermediate position to an open position, whereby fluid within the syringes will be caused to flow into said third passageway of said delivery tube via said outlets of said first and second passageways.

25. A device as defined in claim 24 in which said trigger means is connected to said plunger engaging means for moving said plunger engaging means upon said trigger means moving from said third position toward said fourth position.

* * * * *